United States Patent
Elliott et al.

(10) Patent No.: US 8,711,342 B2
(45) Date of Patent: Apr. 29, 2014

(54) PHOTOACOUSTIC JOULEMETER UTILIZING BEAM DEFLECTION TECHNIQUE

(75) Inventors: William Rowe Elliott, San Antonio, TX (US); Randolph D. Glickman, San Antonio, TX (US); Norman Barsalou, Converse, TX (US); Saher M. Maswadi, San Antonio, TX (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 494 days.

(21) Appl. No.: 12/672,361

(22) PCT Filed: Aug. 11, 2008

(86) PCT No.: PCT/US2008/009597
§ 371 (c)(1),
(2), (4) Date: Sep. 20, 2011

(87) PCT Pub. No.: WO2009/023173
PCT Pub. Date: Feb. 19, 2009

(65) Prior Publication Data
US 2012/0002193 A1  Jan. 5, 2012

Related U.S. Application Data

(60) Provisional application No. 60/955,275, filed on Aug. 10, 2007.

(51) Int. Cl.
*G01J 1/00* (2006.01)

(52) U.S. Cl.
USPC ........... 356/121; 356/434; 356/213; 356/432; 435/287.5; 250/336.1; 600/407

(58) Field of Classification Search
USPC ................ 356/121, 434, 432, 213; 435/287.5
See application file for complete search history.

(56) References Cited

U.S. PATENT DOCUMENTS

| 4,381,148 | A | * | 4/1983 | Ulrich et al. ................. 356/213 |
| 4,652,120 | A | * | 3/1987 | Sell .................................. 356/28 |
| 5,268,746 | A | | 12/1993 | Masetti |
| 6,709,857 | B2 | * | 3/2004 | Bachur, Jr. ................. 435/288.7 |
| 7,057,729 | B2 | * | 6/2006 | Yamaguchi et al. .......... 356/432 |
| 2002/0197708 | A1 | | 12/2002 | Bachur |
| 2006/0055932 | A1 | | 3/2006 | McCandless |

FOREIGN PATENT DOCUMENTS

| JP | 62-039729 | 2/1987 |
| JP | 2003-130827 | 5/2003 |
| JP | 2004-020262 | 1/2004 |

* cited by examiner

*Primary Examiner* — Tarifur Chowdhury
*Assistant Examiner* — Isiaka Akanbi
(74) *Attorney, Agent, or Firm* — Morgan, Lewis & Bockius LLP

(57) ABSTRACT

A joulemeter is capable of non-destructively measuring multiple characteristics of a laser beam. The joulemeter comprises a series of parallel probe beams, which are directed though a transparent media adjacent to an absorbing media that the tested beams pass through. Arrays of optical sensors or a chirp sensor are used to intercept and measure deflections the probe beams. A control unit renders measurements on selected properties of the laser.

23 Claims, 5 Drawing Sheets

PHOTOACOUSTIC JOULEMETER UTILIZING BEAM DEFLECTION TECHNIQUE

RELATED APPLICATIONS

The present application is a U.S. National Phase Application of International Application No. PCT/US2008/009597 (filed 11 Aug. 2008), which claims priority to U.S. Provisional Patent Application No. 60/955,275 (filed 10 Aug. 2007), all of which are hereby incorporated by reference in their entirety.

STATEMENT OF GOVERNMENT INTEREST

This invention was made with government support under Contract N66001-03-D-2501 awarded by the U.S. Army Medical Research Acquisition Activity. The government has certain rights in the invention.

BACKGROUND OF THE INVENTION

The invention relates generally to energy measurement, and more specifically to an apparatus and method for performing radiometric measurements of laser or electromagnetic radiation (EMR).

It is often desirable to determine the total energy output and operational parameters for a source of electromagnetic radiation, such as continuous wave, pulse or high power lasers. Various measurement devices have been developed for this purpose, which typically use thermal or photonic detectors.

Thermal detectors operate by absorbing input radiation, which produces a temperature rise on the detector surface and changes some property of the detector, such as resistance, contact potential, or polarization. The simplest form of thermal detection works by intercepting a laser beam with a material of known thermal properties and measuring the absorbed energy in the form of heat. Calorimeters of this sort are indiscriminate in the type of energy they absorb and can be made sensitive enough to measure small changes in temperature for small masses of absorbing material. However, a major disadvantage of this type of meter is the slow response time. Additionally, there must be a cooling period between measurements to allow for the dissipation of residual heat produced in the previous measurement.

A thermopile is a type of thermal detector that can be used to measure thermal radiation. A thermopile is made up of thermocouple junction pairs connected either in series or in parallel. The resulting transducer converts thermal energy directly into electrical energy. Absorption of thermal radiation by one of the thermocouple junctions, called the active junction, increases its temperature. The differential temperature between the active junction and a reference junction, kept at a fixed temperature, produces an electromotive force directly proportional to the differential temperature created. This effect is called a thermoelectric effect.

A thermocouple consists of two different materials which are connected at one end, while the other two ends are attached to a voltage meter. If there is a temperature difference between the common junction and the voltmeter ends, a thermovoltage is shown by the meter. The magnitude of the voltage is a function of the temperature difference, but also dependent on the nature of the two employed materials. In a thermopile, an absorbing material is attached to the active junction and it is placed in the path of an incident radiation source. The absorber collects the incident heat and the absorber, along with the thermocouple active junction, warm up due to the incident radiation. After a short period, the temperature difference between the active junction and the reference junction will stabilize. The thermocouple material in turn converts the temperature difference into a voltage shown by the voltmeter. Thus, the voltmeter reading is a direct measure of the object temperature. This method does not need any mechanics and can accurately sense static signals. Although thermopiles are independent of wavelength, their major disadvantage is a slow response time. Consequently, thermopiles are primarily used to measure slow pulsed or continuous wave laser systems only.

A pyroelectric detector, another type of device for performing radiometric measurements of electromagnetic radiation, is based on the unique properties of asymmetric crystals, which form a surface charge when heated or illuminated by electro-magnetic radiation. As long as the pulsed or chopped incident radiation is slower than the thermal relaxation time of the crystal, the crystal remains in thermal equilibrium and generates a small amount of current from the crystal. If the chopping or pulsing time of the incident laser energy is shorter than the thermal relaxation time of the crystal, then the crystal heats up and causes more current to flow. Pyroelectric detectors can measure laser events as short as a few picoseconds. They are spectrally similar to thermopiles, making them useful for visible and infrared light measurements. These devices, like thermopiles, operate at room temperature, and require some form of amplification of the generated signal. In summary, in order for a thermal detector to capture all of the incident energy, the incident beam is required to terminate upon reaching the surface of a detector, and thus eliminate any further use of the incident beam.

Another class of laser power meters are photonic detectors. This category of detectors can be further grouped into photoconductive, photovoltaic and photoemissive detectors. A photonics detector responds to the number of individual photon incidents onto its active surface. They normally have a relatively high responsivity and fast response time. However, their responsivity is typically wavelength dependent and tends to have very low damage threshold in comparison to the thermal detectors.

Photoconductive detectors that are used for measuring laser beams are made from specifically designed and doped semiconductor materials. When the photonic energy exceeds the valence levels, the semiconductor produces an electron hole, which is swept away into a conduction band. In simple terms, the incident energy of a laser beam increases the conductivity of the material and more current flows. The required energy states ($E=h\nu$) can vary with the constituent properties of the materials. Depending upon the semiconductor materials used, these devices can be used to sense radiation at wavelengths of less than one µm or longer infra-red wavelengths of 12-25 µm. Normally, photoconductive semiconductors require cooling for longer wavelengths. Some even require cooling at the shorter (3 µm) wavelengths for increased sensitivity. The speed of these detectors varies as a function of the operating temperature, i.e.; the cooler the detector, the faster the response Photoconductive detectors using silicon have response times as fast as a few picoseconds. If cadmium, germanium, lead and indium based materials are used, these devices typically have a response time measured in microseconds or milliseconds. However, like thermal detectors, photoconductive detectors require the laser beam to impinge upon the semiconductor surface and render the measured pulse unusable after a measurement is made.

Photovoltaic detectors are doped semiconductors and can best be described as a diode with a detector on one side. The diode becomes reverse biased when struck by laser radiation.

It conducts current proportionally through a junction and produces a voltage, which is directly related to the amount of incident laser energy or power. Photovoltaic detectors are often called photodiodes. Photovoltaic detectors use some of the same materials as photoconductive detectors, with silicon being the most prevalently used. Silicon photodiodes operate effectively at room temperature (300K), though the best performance can always be achieved by cooling the detector substrate.

Photoemissive detectors operate based on the external photoelectric effect. Photoemisive detectors comprise a surface, typically metal, which releases electrons when struck by photons having an energy value greater than the energy required for an electron to escape the electrostatic barrier presented by the termination of the crystalline material surface. The value of this required energy is known as the work function. Most pure metals have a work function value around 4-5 eV, while other alkali metals have values somewhat lower. If the emitted electron travels through a vacuum with an applied voltage, the device is called a vacuum photodiode. Photoemissive devices can respond to laser energy with wavelengths ranging from 100 nm (UV) to the 1000 nm with higher quantum efficiencies at the shorter wavelengths. Because of the relatively high sensitivities of these devices, and the fact that many electrons are generated for lasers of low energy or operating under continuous wave (CW) mode, the noise generated by the emitted electrons makes it difficult to achieve a wide dynamic range. In addition, as with the aforementioned detector types, the photoemissive detectors rely on the termination of the measured incident radiation.

Most current commercial detectors fall into one of the previously described categories. Therefore, they are limited by one or more of the stated shortcomings, such as low damage threshold, insufficient sensitivity, long response time, long wait time, inability to delivery real-time measurement, or the need for additional parts.

U.S. Pat. No. 4,797,555 to La Mar describes an apparatus that uses a target plate that has a temperature sensitive paint applied on its rear surface. This paint determines the intensity profile of a high energy laser beam. In operation, the front surface of the plate is irradiated by a laser beam. A high speed camera records the isothermal lines formed when the temperature sensitive paint changes from its solid phase to its liquid phase. Isointensity lines are then calculated from the recorded isothermal lines. Although this device provides important data regarding the beam, such as beam profile and intensity, it cannot provide a real-time measurement since the entire laser beam is intercepted by the target plate and transformed into heat. Additionally, cooling time is required between each measurement to dissipate the residual heat from the previous experiment.

U.S. Pat. No. 4,704,030 to Steen teaches a detector to provide in-process beam measurements using a beam deflector set in the path of the beam. An electromechanical transducer is coupled with the deflector to detect mechanical responses of the deflector to an incident beam. One disadvantage of this device is that the accuracy of the detector depends not only on the sensitivity of the electromechanical transducer, but also on its location and the spot size of the beam.

U.S. Pat. No. 4,548,496 discloses a non-destructive laser beam sampling meter whose operation is based on optogalvanic effect, the change in impedance of a gas when exposed to a radiation source such as a laser, in the space between the electrodes of a glow discharge. The device is made to operate on the left side of the Paschen curve, where break down voltage increases with decreasing pressure. The meter is capable of measuring the power of a beam without blocking or unduly perturbing the beam. However, the meter requires a gas chamber which can be filled or evacuated to the desired pressure with an inert working gas. In addition, because the gas chamber is filled and emptied for each measurement, the device has to be precisely recalibrated.

UK Pat. No. 1,127,818 teaches a meter based on the charge effect induced in a piezoelectric crystal illuminated by electromagnetic radiation. However, as with calorimeters, such a device intercepts the entire beam and cannot provide real-time measurements.

U.S. Pat. No. 4,325,252 to Miller et al and U.S. Pat. No. 4,381,148 to Ulrich et al. disclose two methods for non-destructive measurement of laser power by detecting changing gas pressure. Ulrich et al. teaches a device that measures the power of a laser pulse using a gas cell. The gas cell is filled with a radiation-absorbing species that is small enough to allow the laser beam to pass through the cell essentially unaltered. The contraction and expansion of gas within the cell generates acoustic waves which are measured using a microphone. Miller et al. teaches measurement of pressure change within a gas-filled tube as the laser beams passes through. Both designs require a gas cell and a means to pump gas through the cell. In addition, the output voltage of both devices responds to energy density (fluence). Hence, a spot size measurement is required to determine absolute pulse energy. Using ultrasonic transducers or microphones alone to measure the photoacoustic pulse will not provide spot size measurements, so additional instrumentation is required to determine total pulse energy. For example, Ulrich et al. provides an example of a power meter capable of measuring the power of a high energy laser beam using photoacoustic techniques, with minimal destruction of the beam. This power meter includes a cell disposed in the flow path of a gas containing a laser radiation-absorbing species. The absorption coefficient of the absorbing species is small enough to allow the beam to pass though the cell basically unaltered. The concentration of the absorbing species may be varied to modulate its absorption of the laser beam power and produce acoustic waves in the gas, which can be detected and measured to give an absolute measurement of the power in the high energy laser beam. However, because the concentration of radiation-absorbing species needs to be recalibrated for each measurement, it is very difficult to use and cannot provide consecutive real-time measurements. Additionally, Ulrich cannot measure other useful parameters associated with a laser beam, such as spot size or beam profile.

SUMMARY OF THE INVENTION

The instant invention is aimed at solving problems associated with the non-destructive measurement and characterization of laser electromagnetic radiation.

Accordingly, it is the objective of this invention to provide an apparatus and method for accurate, real-time, non-destructive measurements of laser radiation over a wide dynamic range of output energy.

Another objective is to provide an apparatus and method for real-time, non-destructive measurements of operational parameters of a laser beam, including, but not limited to, beam profile, spot size, pulse energy and power.

Still another objective of this invention is to provide an apparatus and method for accurate, real-time, non-destructive measurements of laser radiation in different operational modes, such as pulsed or continuous wave lasers.

Yet another objective is to provide a system which is of low cost to build, maintain and operate.

This invention is a joulemeter that operates based on the combination of the photoacoustic principle, in which light energy is converted into heat, thus producing acoustic or pressure waves in a propagating medium, and photothermal deflection technique (PDT), in which energy as a propagating wave may be measured by deflection of a probe beam. One feature of the invention is the use of multiple parallel probe beams to detect a change in the refractive index of the propagating medium adjacent to the absorptive surface of the detector. The joulemeter of this invention may contain at least one light source that is capable of generating collimated parallel probe beams. These probe beams may be directed through the absorbing medium or a second transparent medium adjacent to and in close proximity to the absorbing media. A matrix of sensors may be located on the other side of the absorbing media positioned to receive the probe beams. As a laser beam passes through the absorbing media, which may be selected based on the laser to be measured, energy from the beam may be converted into heat and may cause propagation of pressure waves that deflect the probe beams.

Changes in the direction and magnitude of the parallel probe beams may be measured by a sensor matrix and are forwarded to a control unit. The control unit may contain data acquisition programs and conversion algorithms. It may receive data collected by the sensors and convert the data into measurements of selected properties of the laser beam, which may include but are not limited to spot size, beam diameter, beam profile, and total energy. Total energy may be determined by integrating the energy within the detected laser spot.

Application of the joulemeter may be extended to a wide range of electromagnetic radiation sources by using absorbing media with different optical absorption coefficients. When a laser with known wavelength is being measured, the absorbing media with the appropriate absorption coefficient may be selected and switched into position for the measurement. Mechanical means may be employed to change the absorbing media. The control unit may also be programmed to select the appropriate absorbing media based on a measurement of the laser wavelength.

Because the absorbing media may be of low absorption coefficient and the laser beam may not be substantially absorbed or split by the joulemeter during measurement, real-time and repeat measurement of the laser output may be possible. In addition, there may be minimal damage to the sensor, which may enable the joulemeter to measure a wide range of laser energies, including high-energy lasers or pulsed lasers.

DESCRIPTION OF THE PREFERRED EMBODIMENTS

This invention relates generally to energy measurement, particularly to an apparatus and method for measuring basic properties of electromagnetic radiation, such as a laser beam.

Figure 1:
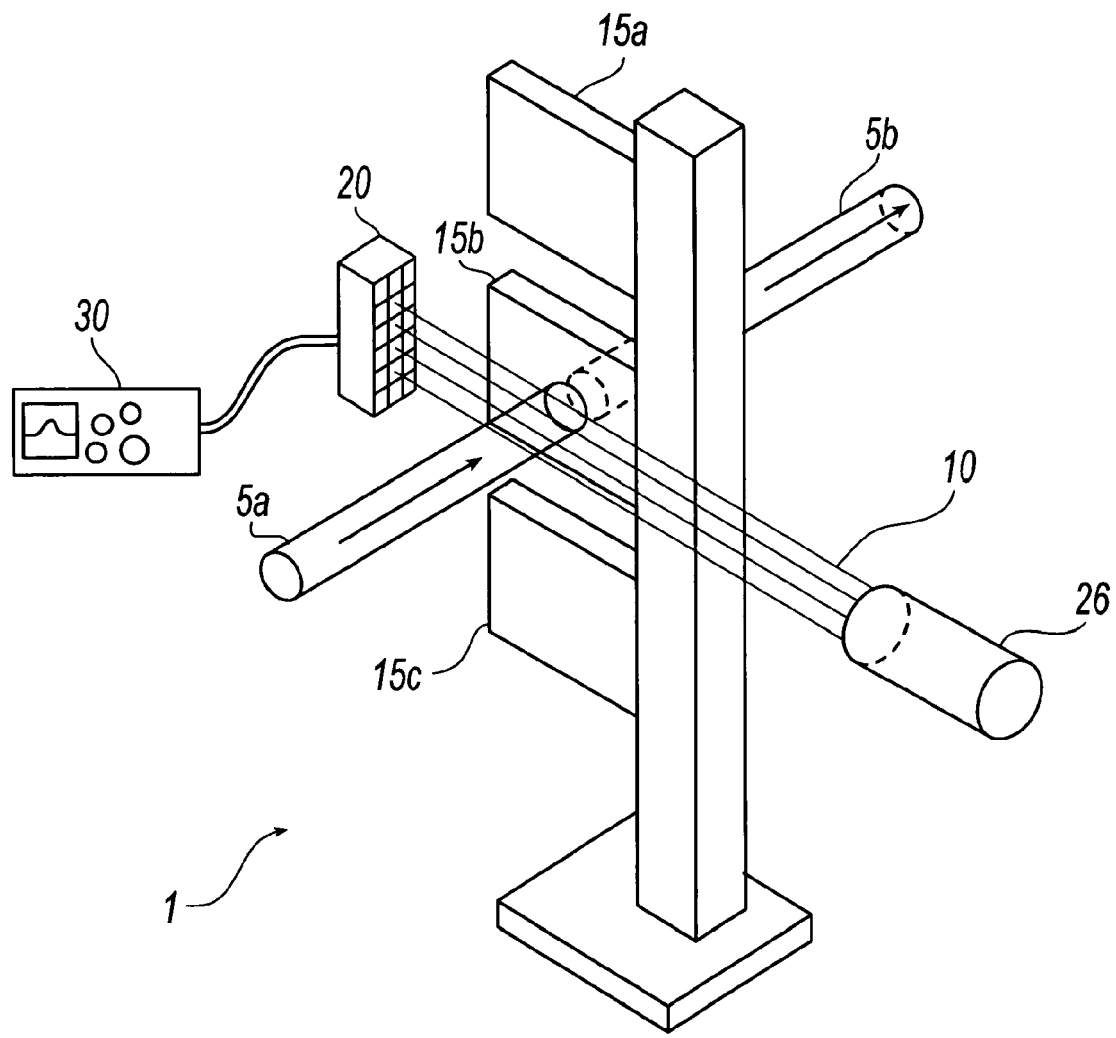
FIG. 1 is a schematic illustration of a photoacoustic joulemeter using the method of the present invention with multiple probe beams.

The current invention may be used to measure properties of laser beams generated by a source operating in either pulse energy or continuous wave (CW) mode. The joulemeter 1 according to one embodiment of the present invention may comprise the following: at least one of absorbing media 15a-c; a series of parallel probe beams 10 which are directed through at least one of the absorbing media 15a-c or a second transparent medium (not shown) closely adjacent to the absorbing media 15a-c; multiple arrays or a matrix of sensors 20; and a control unit 30, as shown in FIG. 1.

One feature of this invention is the non-contact optical implementation of the photothermal deflection technique, which is highly sensitive and capable of providing fast responses. This technique is based on the detection of a refractive index gradient generated by heating the absorbing media. Measurements of the laser beam are carried out by monitoring deflection of parallel probe beams oriented orthogonally to the incident laser beam.

Photoacoustic detection is a measure of acoustic energy that results from the direct conversion of laser energy into heat. The process involves the absorption of energy from a pulse or modulated CW light source by an absorbing element with a low absorption coefficient. For example, for short laser pulses, e.g. Q-switch laser pulses, which have a high peak power, a broad laser beam which is incident along the normal to the interface between a transparent medium with a relatively low absorption coefficient, and an absorbing medium detector surface, whose absorption coefficient is greater than zero, the light to acoustic energy conversion is highest where thermal confinement occurs. The stress or inertial confinement created leads to generation of a pressure wave P, whose density is linearly proportional to the energy density F (energy/beam area) as follows:

where $\alpha$ is the absorption coefficient of the detector surface, c is the acoustic speed in the medium, $\beta$ is the thermal expansion coefficient of the detector surface, $c_p$ is the specific heat of the detector surface, and z is the depth in the detector surface (it is zero since the acoustic wave is generated and propagates to the adjacent medium from the detector surface). All the above parameters remain constant during energy measurements.

Figure 2A:
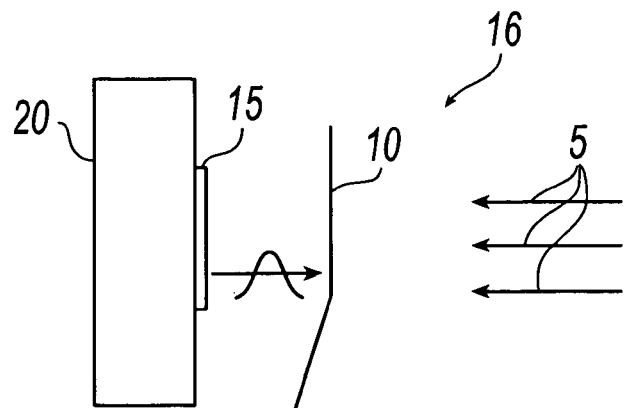
FIG. 2 is a schematic drawing demonstrating the operation of the present invention.
Figure 2B:
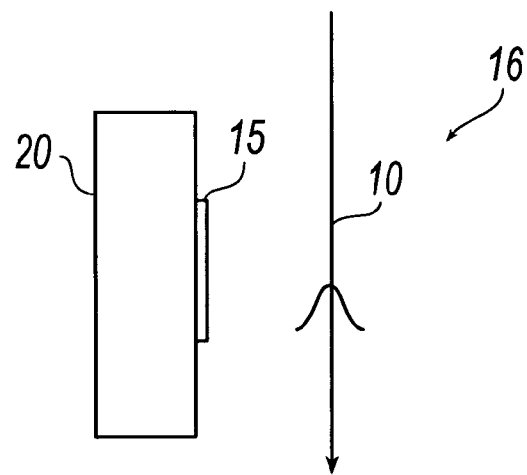
Figure 2C:
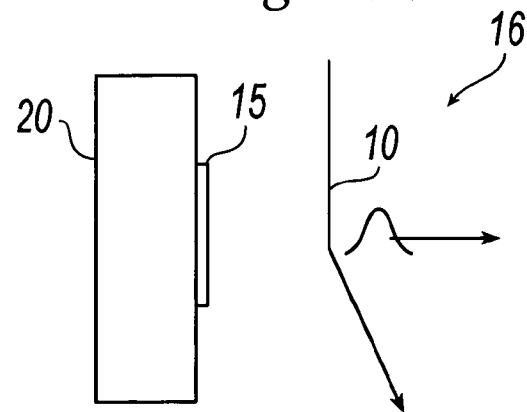

The principle of photothermal deflection is illustrated in FIGS. 2A-C. As a laser beam 5, passes through the absorbing media 15 of the detecting surface 20, a small amount of energy from a pulse or modulated continuous wave light source is absorbed by the absorbing media 15, which creates a variable heat source. Thermal confinement occurs and serves as a source for acoustic or pressure waves 25. The pressure wave travels outward from the surface of the absorbing media 20 and propagates within an adjacent transparent or almost transparent medium 16. The medium 16 may be air, although other, preferably transparent, materials can be used. As the pressure or acoustic waves pass through the medium 16, a refractive index gradient is produced within the transparent media. Laser beams 5 of different power will generate pressure/acoustic waves 25 of different frequency and amplitudes, which in turn cause each probe beam 10 to deflect in various directions and magnitudes. The deflection of the probe beams 10 can be monitored and recorded by photodiode arrays or chirp photodiodes 20 arranged at the opposite side of the probe beam source, and forwarded to a control unit 30 (FIG. 1). The control unit 30, which may be any computational device, such as a microprocessor or a computer, may be used to calculate the specified beam parameters based the known wavelength of the laser beam 5 and the measurements provided by sensor arrays 20.

A preferred embodiment of present invention is shown in FIG. 1. An absorbing media 15 is aligned in the path of an incident laser beam 5. At least one light source 26 is placed on one side of this absorbing media 15. The light source(s) 26 is capable of generating multiple parallel probe beams 10, which are directed through transparent medium 16 adjacent to the absorbing medium 15a-c. An array of photodiodes or a chirp sensor 20 is placed on the other side of the absorbing medium 15 and configured to receive the probe beams 10 without interference to the passing laser beam 5. In FIG. 1, 5a refers to the laser beam before entering the absorbing medium, and 5b refers to the laser beam after entering the absorbing medium. In operation, the probe beams are deflected by acoustic waves propagating through transparent medium 16 adjacent to the surface of the absorbing medium 15. The diode array 20 or chirp sensor intercepts the probe beams 10 and measures the direction and magnitude of deflection of each of probe beams 10 and forward the data to the control unit 30.

Figure 3:
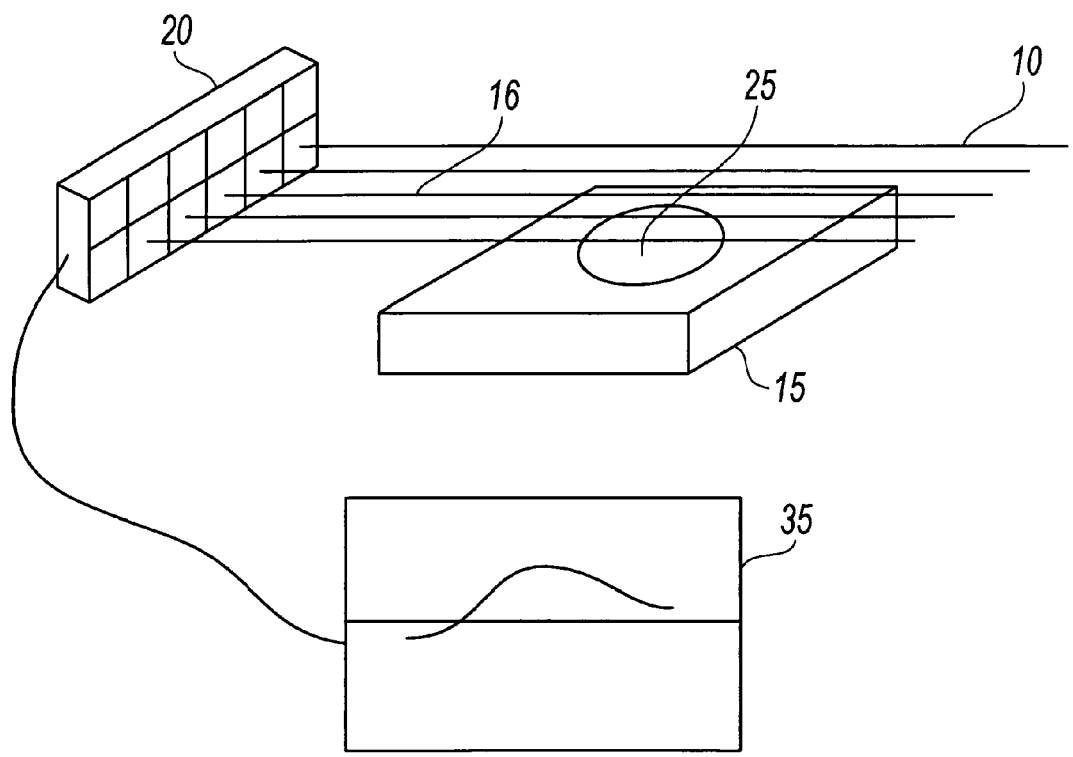
FIG. 3 is a schematic design of a beam profiler/spot size meter according to the present invention.

The control unit 30 then uses these data together with the expected wavelength of the laser system to render measurements on selected properties of the laser, such as beam power, spot size, and beam profile. Laser spot size and a one-dimensional beam profile may be determined based on the position and amplitude of each probe beam signal. The process of creating a one-dimensional beam profile using the joulemeter 1 of the current invention is illustrated in the schematic drawing of FIG. 3. The control unit 30 measures selected properties of the laser, and outputs the data to either an internal or external display device 35, a printer (not shown) or a storage device (not shown). Two-dimensional profiles of the laser beam 5 may also be created by using a net of probe beams 10, which may be constructed by placing two series of parallel probe beams 10 separately in the X and Y directions. As in the one-dimensional measurements, individual probe beams may be deflected as they pass through the refractive index gradient within the second transparent medium 16. Measurements may then be calculated by the control unit 30 and displayed or recorded. One or more light sources may be used to generate the series of parallel probe beams required by the invention. For example, parallel diode lasers may be used to produce a series of parallel probe beams. Alternatively, a single continuous wave laser or a high density LED source may be coupled with multiple fiber optic cables to generate the parallel probe beams. The light source may be collimated and focused using small optical lenses. The resolution of measurements, such as beam profile or spot size, depends on the distance between the probe beams. The smaller the distance between the beams, the higher the spatial resolution for the beam profile and spot size measurements. In one embodiment, the probe beams are set to be less than 1 mm apart.

The absorbing media may be in gas, solid or liquid form. Saline solution, optical glass and inert gas are a few examples of applicable absorbing media. The wavelength of the laser being tested is a determinative factor in deciding the appropriate absorbing media. The wavelength, or expected wavelength of the laser system to be measured needs to be known to ensure that there is no ablation of the media as it absorbs the energy delivered at said wavelength during testing. When the absorbing media is either gas or liquid, it may be contained in a highly transmissive and impermeable cell.

In a preferred embodiment, the absorbing media may be made of optical glass. Most preferably the optical glass may be a doped silicon glass. The glass selected must minimally perturb the laser beam as it passes through the absorbing media for measurement. If the glass is too transmissive at the measurement wavelength, the laser pulse is too weak to produce an acoustic wave. If the glass is too absorbent at the incident wavelength, the energy of the laser may cause ablation of the absorbing media's optical surface. Therefore, the optimal absorption coefficient of absorbing media must be determined and paired with the expected wavelengths of the laser tested.

A wider range of lasers may be measured if the joulemeter contains more than one absorbing medium. Each absorbing medium is best suited for measurement within a specified wavelength range. For example, a number of absorbing media with predetermined properties may be installed in series in a single apparatus and may be interchangeably placed into measurement position via mechanical or other means.

To measure lasers of unknown energy, an automatic calibration may be conducted. The calibration may be initiated using the lowest absorption glass medium for the wavelength under test. If no beam deflection occurs, the medium may be moved out of the beam path and the next piece of glass with a slightly higher absorption coefficient may be positioned in the beam path for the next trial measurement. This process may be repeated until beam deflection can be quantified and subsequently measured after determining the amplitude of each deflected beam. In addition to facilitating the selection of the media of appropriate absorption coefficient, this process may provide physically meaningful information on the distribution of the amplitudes of the probe beams that are being diffracted by the acoustic wave collected during the calibration step.

In practice, assuming that the laser beam being tested is Gaussian and reasonably centered on the apparatus of the invention, it is expected that the center of the laser pulse under test will deflect the center probe beam first as increasingly absorbent media are translated into position. If the center probe beam is deflected sufficiently, then a translation of glass with a higher coefficient of absorption into place may ensure that the center probe beam is deflected more than the previous deflection with the lower absorptive glass. Measurements of the two probe beams immediately adjacent to the center probe beam may also be possible. This process may continue until the beam diameter can be determined, which in turn allows the total integrated energy of the pulse to be determined. However, this process may only be necessary for lasers of unknown pulse energy. For an imbedded application (e.g., medial laser applications) or for use with lasers of a known or expected energy, it may not be necessary to titrate.

Various types of optical sensors or detectors may be used to determine the direction and magnitude of deflection of the probe beams, including but not limited to arrays of photodiodes, complementary metal-oxide semiconductor (CMOS) or charge-coupled device (CCD) chip sensors. Photodiodes may be arranged in small linear arrays or two dimensional focal plane arrays such as those used in digital cameras. However, the array(s) or sensor chip(s) must be large enough so that one probe beam does not cover the whole linear or 2D array.

In a preferred embodiment, the probe beams are either parallel or substantially parallel. However, alternative embodiments of the invention may use other geometric configurations for the plurality of probe beams in order to measure characteristics of the laser or electromagnetic radiation beam. For example, the probe beams of this invention may be converging, diverging, intersecting, orthogonal, or skew lines.

This second transparent media may be a gas, liquid or solid with very low absorption coefficient, such as air. Ideally, the surface of the second transparent media needs to have an absorption coefficient that is smaller than the surface absorption coefficient of the absorbing media. It is also desirable to have similar physical and acoustic properties in order to reduce the mismatch. In a preferred embodiment, the transparent media is a gas, such as air.

A control unit may be included in the system. The control unit may be any computational device including but not limited to a microprocessor or a computer. In operation, photodetectors or photosensors may forward the measured data either directly or via a signal amplifier to the control unit, which is loaded with data acquisition program and algorithms required to process the data. The control unit may then perform the calculation based on these measurements, as well as the previously entered wavelength of the testing laser, and renders selected measurements regarding the laser. The selected measurements may then be output to a display device, which may be an integrated or separate display device, a printer or a storage device. In addition, information regarding different absorbing media and their corresponding wavelengths may also be stored in the control unit. Control units may select the appropriate absorbing media based on the expected wavelength of each testing laser and the stored information, and then issue a command to the mechanical means, which in turn switches the appropriate absorbing media in position.

The joulemeter of the current invention can also be used to measure the intensity of a continuous wave laser source using the same method that is used to measure pulse laser energy. However, the incoming CW laser beam must be chopped or modulated through a controlled mechanism. As discussed previously, photoacoustic power meters that use microphones or acoustic transducers as sensors of acoustic waves typically incorporate an optical chopper in their acoustic cell. However, if the laser power is high, damage to the acoustic cell or the optical chopper will occur.

Figure 4:
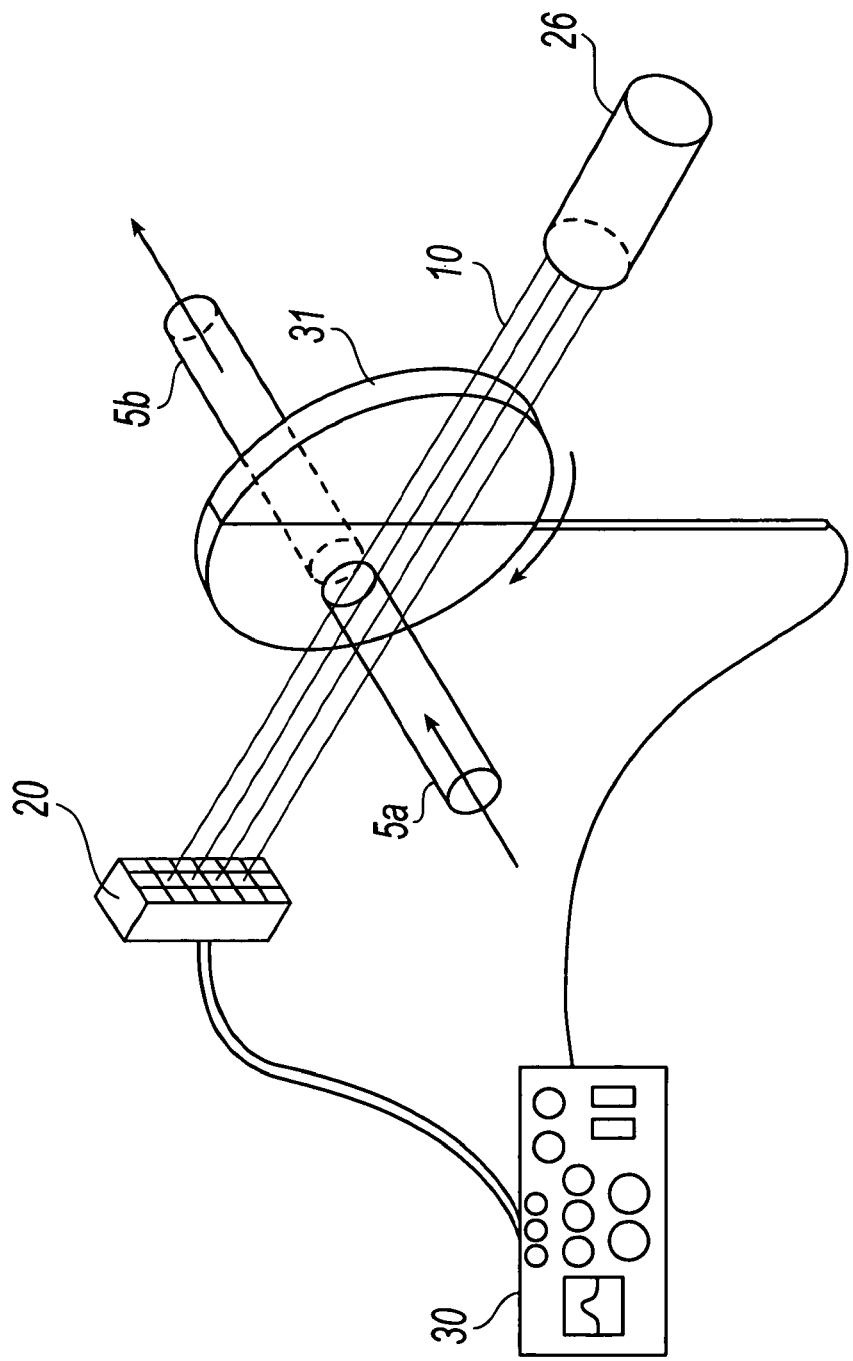
FIG. 4 is an embodiment of the present invention with a rotating disk sensor for measurement of continuous wave (CW) lasers using the present invention.

In this invention a photoacoustic converter is used. This photoacoustic converter may comprise an absorbing media with two or more regions of different absorption coefficients. In an embodiment, a disk-shaped absorbing media may be divided into two or more regions. Each region of the absorbing media may have a different absorption coefficient. This disk absorbing media may be operatively connected to a rotation means, such as a motor or a rotor. As shown in FIG. 4, during operation, the absorbing media disk 31 is set to rotate at a predetermined frequency and the heat generated from the absorption of the CW laser radiation 5 is modulated by the rotation of the disk 31. At very high laser power, absorbing media disk 31 can be made of doped fused silica or glass with absorbing molecules of certain chromophores at different concentrations creating a medium with different absorption coefficients at different areas.

Figure 5:
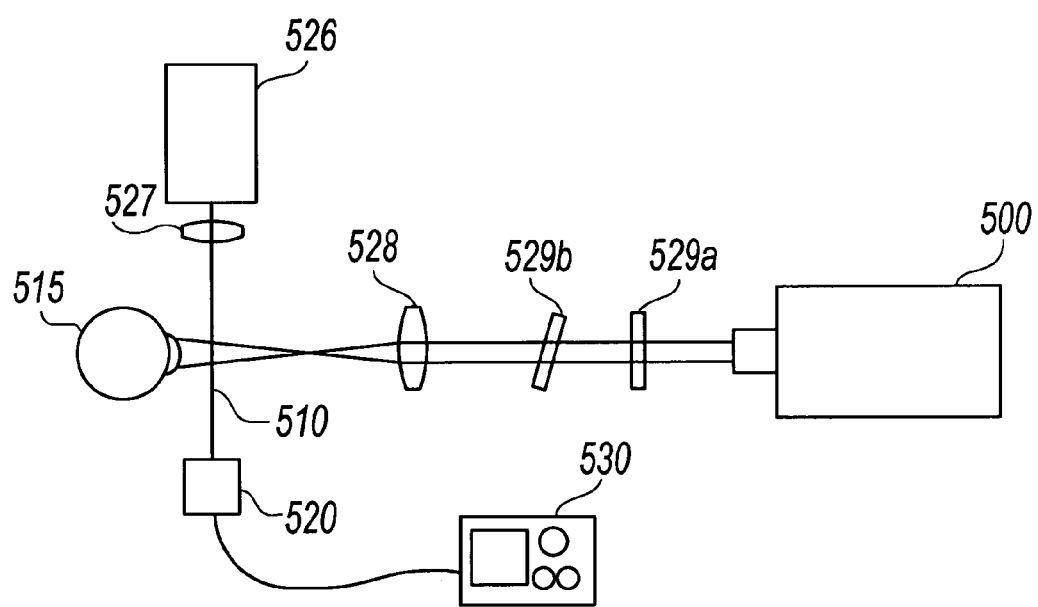
FIG. 5 is an example of an application of the present invention.

A representative application of the present invention is shown in FIG. 5. This application uses the joulemeter of the present invention to determine drug distribution in a patient's eye 515, although it could be used for measuring drug distribution in other parts of a patient's body. A pumped tunable optical parameter oscillator (OPO) laser 500 shoots a beam 505 through attenuators 529a-b, which ensure that beam 505 is not of such strength that it damages the patient's eye 515. The beam is then focused by lens 528.

Upon striking the eye 515, beam 505 generates a photoacoustical signal based on the specific spectral agent of the material or pharmocological agent being detected. When those molecules absorb light, their temperatures and volumes increase as do their volume. The pressure wave propagated by this increase in temperature and volume deflects probe parallel beams 510 emitted by light source 526. An array of photodiodes or chirp sensor 520 on the other side of eye 515 from light source 526 intercepts probe beams 510 and measures the direction and magnitude of deflection of each of probe beams 510 and forwards the data to control unit 530. Control unit 520 processes the data to determine the drug distribution in eye 515.

The present invention may be used in a wide range of embodiments in conjunction with a large number of laser or electromagnetic beam applications.

For example, the invention may be used to monitor and control lasers or other electromagnetic beams used in medical diagnosis or treatment of a human or animal patient. In many medical applications, precise applications of laser power and particular beam characteristics are desired in order to perform the desired function without excessively harming patient tissue or causing other harmful effects associated with excessive exposure to laser light. Such applications include lithotripsy, photo-coagulation, photo-ablative therapies, surgical applications, in vivo quantitation of pharmaceutical concentrations (e.g., in the eye), blood-borne pathogen detection, nerve stimulation, and targeted destruction of pathogenic organisms or cancerous or otherwise undesired cells. A laser monitored by the invention could be utilized in therapies in combination with pharmacological agents sensitive to a particular wavelength to target the activity of the pharmacological agent to particular cells or tissues by directing the laser to those cells or tissues, or conversely by using pharmacological agents specific to particular cells or tissues (such as cancer cells) to target the effects of the laser beam to those cells or tissues.

The invention may be used in conjunction with a high energy laser or electromagnetic beam. Precise control and standardization of laser beam intensity in high energy laser applications has proven difficult because most existing methods for measuring high energy laser intensity require not only interruption of the beam, but destruction of the target material, making real-time monitoring of laser power impossible. The present invention could be used to precisely adjust beam characteristics, including beam diameter, energy density, beam profile, spot size, and pulse energy, to match the desired impact on the beam target, or to adjust to varying environmental conditions such as atmospheric conditions. In particular, the present invention may be utilized as a monitoring and control device for a directed energy weapon (DEW). The present invention could be used to monitor and control DEWs designed to monitor, range, track, target, damage, disable, destroy, deflect or interfere with a variety of targets, such as ground vehicles, buildings, aerial or exo-atmospheric vehicles such as aircraft or ballistic missiles, surface or submersible vessels, projectiles such as artillery rounds, and command, control, communications, computer systems and information ($C^4I$) equipment. DEWs utilizing the present invention could be directed against human or animal targets either for lethal purposes or non-lethal applications such as riot control or communication. With the precise control of laser or electromagnetic energy beam characteristics and intensity provided by the invention, a single DEW could be used for a range of tasks requiring differing intensity levels and beam characteristics. Enabling multiple uses of a single directed energy beam device could be of particular importance when a small or lightweight device is desired, such as when the device is mounted on a vehicle (including a ground, sea, air, submersible or exo-atmospheric vehicle) or carried by a human or animal.

The present invention could further be used in lasers or electromagnetic energy beams in a wide range of industrial applications. Such applications include: materials conditioning processes such as welding and machining, monitoring pharmaceutical, chemical, or food products for quality control in manufacturing, shelf life, and presence of contaminants, and use in electronic devices.

A device according to the present invention could also be used in numerous laboratory applications, such as laser-based fluorescence microscopy (where it is desired to avoid effects such as photobleaching and phototoxicity associated with excessive laser exposure), detection of chemical, biological, or nuclear (CBN) agents, or in any experiment in which it is desired to hold the characteristics of a laser or other electromagnetic radiation beam constant in order to isolate some other variable.

The joulemeter is capable of being used in National Board of Standards (NBS) calibration for high energy lasers. The current NBS standards define a laser to be "high energy" if the laser produces 300 J or more per pulse and requires direct observation of the incident pulse on a piece of specified material

What is claimed:

1. A joulemeter for non-destructively measuring electromagnetic radiation, comprising:
   a plurality of absorbing media aligned with an electromagnetic radiation source such that a beam generated by said radiation source passes through at least one of said plurality of absorbing media;
   at least one light or electromagnetic radiation source capable of generating a plurality of probe beams, wherein said probe beams are directed through the absorbing media or a second medium adjacent to said absorbing media;
   at least one sensor positioned to receive and measure said probe beams, wherein said sensor does not obstruct said electromagnetic radiation beam;
   a control unit that selects an absorbing media based on the expected wavelength of said electromagnetic radiation and is configured to receive signals from said sensor or sensors, and convert the output into measurements of selected characteristics of the beam.

2. The joulemeter of claim 1, wherein the source of said electromagnetic radiation is a laser.

3. The joulemeter of claim 2, wherein said laser is a high energy laser, a pulse laser, or a continuous wave laser.

4. The joulemeter of claim 1, wherein said absorbing media is a solid, liquid or gas.

5. The joulemeter of claim 1, wherein said probe beams run substantially parallel to one another.

6. The joulemeter of claim 1, wherein said plurality of absorbing media are housed on a circular plate.

7. The joulemeter of claim 1, wherein said control unit is loaded with at least one data acquisition program and at least one signal processing algorithm.

8. The joulemeter of claim 1, wherein a mechanical means aligns at least one of said selected absorbing media in path of said beam.

9. The joulemeter of claim 8, wherein said mechanical means comprises a motor or a rotor.

10. The joulemeter of claim 1, wherein said light or electromagnetic radiation source is at least one laser.

11. The joulemeter of claim 10, wherein said laser is a continuous wave laser or a diode laser.

12. The joulemeter of claim 11, wherein said continuous wave laser is coupled with at least one fiber optic fiber.

13. The joulemeter of claim 1, wherein said sensor is selected from the group consisting of:
   at least one photodiode;
   at least one chirp photodiode;
   a CCD photosensor;
   a CMOS photosensor; or
   a quad photodetector.

14. The joulemeter of claim 13, wherein said photodiodes are arranged as a matrix.

15. The joulemeter of claim 1, wherein said control unit receives data from said sensors, and outputs measurements of at least one laser property selected from the group consisting of:
   pulse energy;
   beam diameter;
   energy density;
   beam power;
   beam profiling; and
   spot size.

16. The joulemeter of claim 1, further comprising at least one signal processor.

17. The joulemeter of claim 16, wherein said signal processor comprises:
   a signal amplifier; or
   an electronic filter.

18. The joulemeter of claim 1, wherein said electromagnetic radiation is a continuous wave energy source, wherein said absorbing medium is disk-shaped and comprises at least two regions of different absorption coefficients.

19. The joulemeter of claim 18, wherein said disk-shaped absorption medium comprises fused silica or glass doped with different concentrations of absorbing molecules of chromophores in at least two different regions.

20. A method of measuring selected properties of a pulse laser beam, comprising the steps of:
   selecting an absorption media based on the power of the laser beam to be measured and the absorption coefficient of each glass;
   positioning absorbing media in the path of said electromagnetic beam;
   directing a plurality of probe beams in a second media adjacent to said absorbing media;
   measuring probe beam deflections using at least one sensor positioned to receive probe beams, wherein said sensor does not obstruct said electromagnetic radiation beam;
   rendering measurements on at least one of said selected properties of said electromagnetic radiation.

21. A method according to claim 20, wherein said selected properties comprise at least one of:
   beam diameter;
   energy density;
   energy profile; and
   beam profile.

22. A method of measuring selected properties of a continuous wave electromagnetic radiation beam, comprising the steps of:
   modulating said continuous wave electromagnetic radiation beam with a disk-shaped absorption medium, wherein
   at least two regions of said disk-shaped absorption media have different absorption coefficients, and
   said disk-shaped absorption media is rotated at a known frequency;
   positioning an absorption medium in the path of said electromagnetic radiation beam;
   directing a plurality of probe beams in a second medium adjacent to said absorbing medium;
   measuring probe beam deflections using at least one sensor positioned to receive and measure said probe beams, wherein said sensor does not obstruct said electromagnetic radiation beam;

rendering measurements on at least one of said selected properties of said electromagnetic radiation beam, wherein said selected properties are selected from the list consisting of:
pulse energy;
beam diameter;
energy density;
beam power;
beam profiling; and
spot size.

23. A method of controlling the beam characteristics of a laser or electromagnetic radiation beam, comprising the steps of
positioning disk shaped absorbing media, said disk-shaped absorbing media comprising at least two regions of different absorption coefficients, in the path of said laser or electromagnetic radiation beam;
directing a plurality of probe beams in a second media adjacent to said absorbing media;
measuring probe beam deflections using at least one sensor positioned to receive probe beams, wherein said sensor does not obstruct said laser or electromagnetic radiation beam;
rendering measurements on at least one of said selected characteristics of said laser or electromagnetic radiation beam; and
modulating control parameters of the laser or electromagnetic radiation beam in order to match the measured beam characteristics to the desired beam characteristics, wherein said beam characteristics are selected from the list consisting of:
pulse energy;
beam diameter;
energy density;
beam power;
beam profiling; and
spot size.

* * * * *